United States Patent [19]

Hara

[11] 4,033,356

[45] July 5, 1977

[54] APPARATUS FOR THERAPEUTICAL TREATMENT AND STIMULATION OF MUSCLES BY LOW-FREQUENCY OSCILLATING ELECTRIC CURRENT

[75] Inventor: Takaaki Hara, Tokyo, Japan

[73] Assignee: Hakuju Institute for Health Science Co., Ltd., Japan

[22] Filed: Aug. 20, 1975

[21] Appl. No.: 606,091

[52] U.S. Cl. .............................. 128/405; 128/410; 128/411; 128/422

[51] Int. Cl.² ........................................... A61N 1/04

[58] Field of Search .......... 128/404, 405, 406, 409, 128/410, 411, 416, 417, 418, 421, 422, 2.1 R, 24.1–24.5

[56] References Cited

UNITED STATES PATENTS

| | | | |
|---|---|---|---|
| 1,935,138 | 11/1933 | Windisch | 128/410 |
| 2,659,372 | 11/1953 | Andresen | 128/406 |
| 2,842,136 | 7/1958 | Browner | 128/410 |
| 3,025,858 | 3/1962 | Browner | 128/410 |
| 3,107,672 | 10/1963 | Hofmann | 128/405 |
| 3,424,165 | 1/1965 | Moss | 128/405 |
| 3,472,233 | 10/1969 | Sarbacher | 128/422 |
| 3,520,187 | 7/1970 | Petersen | 128/2.1 R |

Primary Examiner—William E. Kamm
Attorney, Agent, or Firm—Larson, Taylor and Hinds

[57] ABSTRACT

An apparatus for therapeutical treatment and stimulation of muscles in a human body comprises a housing containing a low-frequency oscillating electric circuit having dry cells as power source and an electrode section having two electrodes electrically connected and replaceably associated with the housing. The apparatus has a construction of compact and small size adapted for therapeutical and stimulating treatment by electric charge applied to the muscles with the electrode section contacted to muscle portions so as to remedy pain and fatigue in the muscles and strengthen the muscles by stimulation.

3 Claims, 22 Drawing Figures

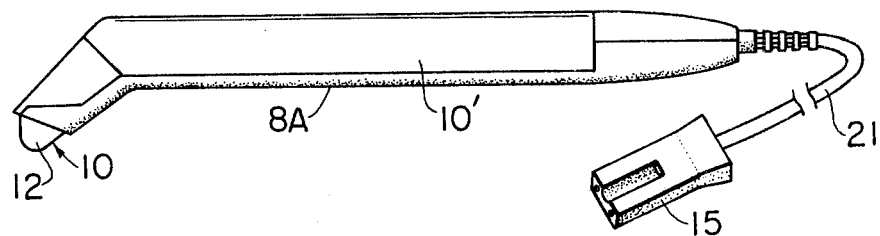
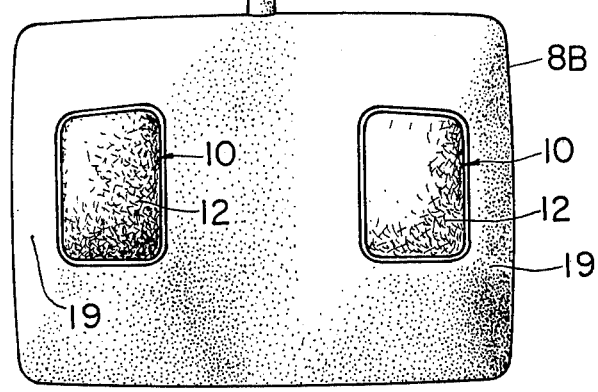
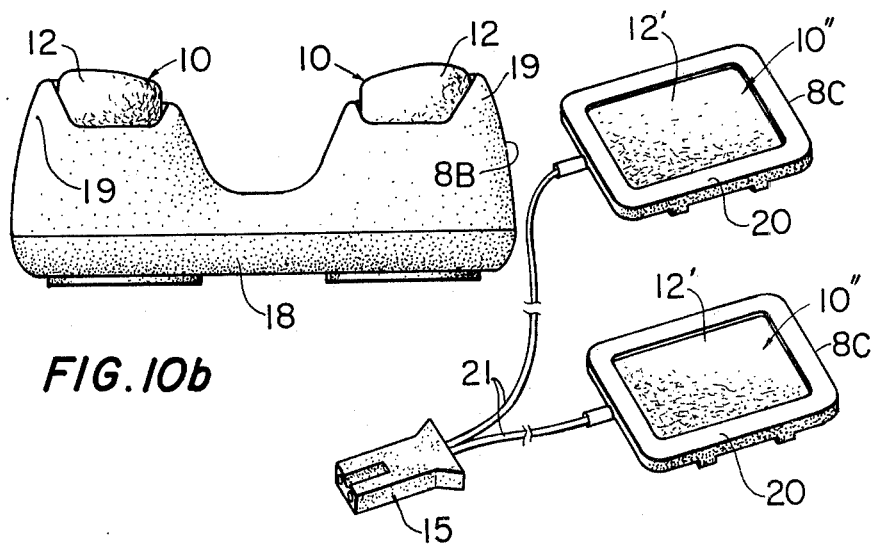

APPARATUS FOR THERAPEUTICAL TREATMENT AND STIMULATION OF MUSCLES BY LOW-FREQUENCY OSCILLATING ELECTRIC CURRENT

BACKGROUND OF THE INVENTION

Low-frequency therapeutical apparatuses hitherto used for treating muscles of a human body have been directed solely to the remedy of pain and fatigue in the muscles but not to the positive treatment of the muscles by means of stimulation. Although necessary physical excercise or training of muscles is recognized as important so as to keep the health and strength of a body, such excercise or training is extremely limited in modern social life. It is known that the physical action of a body mostly derives from muscle movement of body frame as well as of internal organs and, if a man neglects physical exercise or training, the muscles will not function but will rather become atrophied or withered. The muscles which are functionally disabled due to sickness or fracture of bones are heavily withered and thereby cause dull or slow motion of a body. Excess movement or training as would produce fatigue in the muscles, which may further grow and produce pain in the body resulting in other troubles.

It is also known that stimulation of muscles by charging electricity by use of low-frequency oscillating circuit may cause excitation and contraction of muscles which are then slackened as the electric supply in interrupted. Thus, by repeating the intermittent electric charge it is possible to give the muscles a recoverying effect.

When certain portions of muscles may suffer from pain, such muscles are not good in circulation of blood and will become stiffened by tension. The described electric charge may provide adequate stimulus to the muscles and better circulation of blood so that the muscles may become softened and the pain can be removed. In the similar manner, the fatigue in the muscles may be removed by stimulation or excitation of the muscles by electric charge adequately applied to obtain better circulation of the blood.

Beside the above therapeutical treatment by means of low-frequency oscillating circuit, it is found that the apparatus using such low-frequency oscillating cirucit is also available for positive increase in the acitvity of muscles, since it is known that the muscles may be strengthened by being positively trained by repeating application of intermittent electric charge to provide stimulus and excitation, or otherwise slackening in the muscles. Removal of fatigue and pain as well as positive stimulation in the muscles can thus be provided by means of a simple device used effectively in daily life which can also serve for the maintenance of constant health.

BRIEF SUMMARY OF THE INVENTION

The invention relates to an apparatus for therapeutical treatment and stimulation of muscles in a human body by means of a low-frequency electric current.

The apparatus according to the invention provides an electric and therapeutical treatment of muscles in a human body by using an electric current of a value most adapted for a human body, remmoving fatigue and withering and besides positively stimulating the muscles for strengthening.

The removal of fatigue and withering of muscles as well as positive stimulation and training of muscles may be achieved effectively by the apparatus of the invention, which essentially comprises a housing containing a low-frequency oscillating electric circuit having dry cells as a power source and an electrode section having two electrodes electrically connected and replaceably associated with the housing. The apparatus is constructed in a compact small size adapted for therapeutical and stimulating treatment applied to the muscles with the electrode section brought into contact with portions of the muscles so as to remedy pain and fatigue in the muscles and strengthen the musles by stimulation.

Therefore, a primary object of the invention is to provide an apparatus for therapeutical treatment and stimulation of muscles by low-frequency oscillating electric current, which can serve most effectively as electrical and therapeutical device in use of low-frequency electric oscillating circuit.

Another object of the invention is to provide the apparatus as defined above, which provides positive stimulation and excitation as desired to any portion of the muscles, training and strengthening of the muscles in that portion so as to realize health and beauty in the body by means of the low-frequency oscillating current.

Another object of the invention is to provide the apparatus as defined, which can be operated simply and readily by hand and which is easily portable anywhere by the operator.

A still another object of the invention is to provide the apparatus as defined, which comprises a housing containing an electrode section having two replaceable electrodes suited to provide the electrical and therapuetical treatment to the muscles in any portion of a body.

These and other objects and advantages of the invention can be realized as a whole by the construction and by suitable operation of the apparatus of the invention, which will be clear from the following description given by way of example on various embodiments as referred to the accompanying drawings.

It is to be understood that any modification of variation may be made with regard to the construction and the circuit so far as they do not depart from the spirit or scope of the present invention.

BRIEF DESCRIPTION OF THE DRAWINGS

FIG. 5a is a plan view of a sponge member and FIG. 5b a front view of the sponge member shown in FIG. 5a;

FIG. 7 is a diagrammatic view of output waves of the oxcillating circuit shown in FIG. 6 and FIG. 6a;

FIG. 9 is a plan view of another electrode section replaced in the apparatus of the invention;

FIG. 10a is a plan view of another electrode section and FIG. 10b a front view of the electrode section shown in FIG. 10a; and FIG. 11 is a perspective view of another electrode section.

DESCRIPTION OF THE INVENTION IN RELATION TO DRAWINGS

The apparatus of the invention will now be described below with reference to the accompanying drawings.

Figure 1:
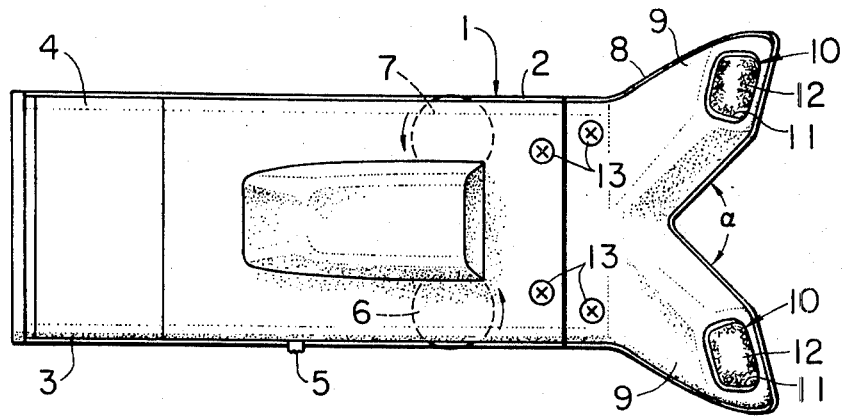
FIG. 1 is a plan view showing an embodiment of an apparatus according to the invention.
Figure 2:
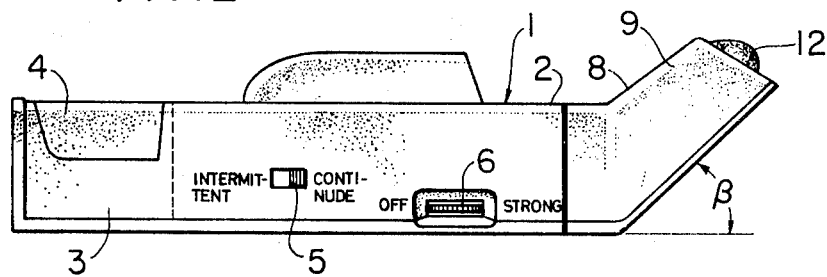
FIG. 2 is a front elevation of the apparatus shownin FIG. 1.

FIGS. 1 and 2 illustrate an embodiment of the invention, in which 1 denotes a low-frequency electrical therapeutical apparatus, which comprises a housing 2 and an electrode section 8 containing two electrodes. The housing 2 includes a cell part 3 and a cover plate 4 for the cell part 3. It also includes a slide switch 5 for intermittent switching, a variable resistor 6 with an output switch, and a variable resistor 7 for adjustment of the frequencies of the current waves. In the housing 2, there is provided a low-frequency oscillating circuit.

Figure 3:
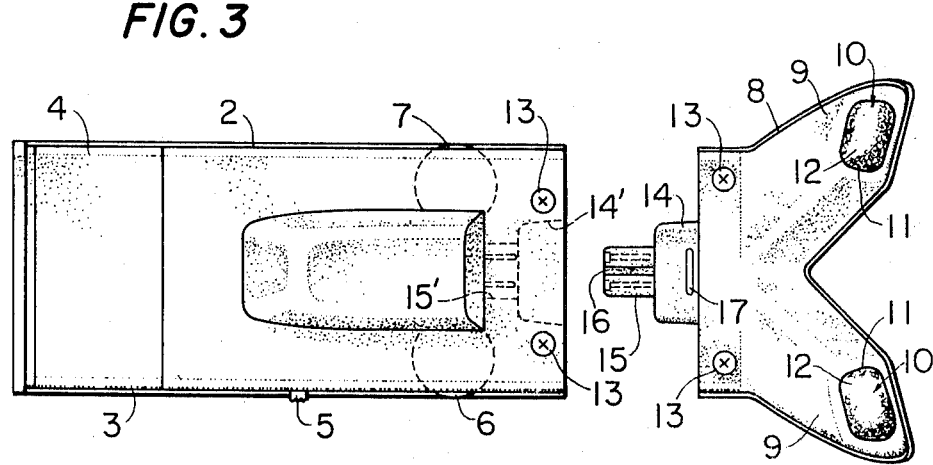
FIG. 3 is the apparatus shown in plan view, in which the electrode section is displaced from the housing of the apparatus.

The electrode section 8 has two arms 9, 9 and two electrodes 10, 10 provided at the ends of the arms 9, 9. The arms 9, 9 are disposed in position such that they will make an angle $\alpha$ between each other (as shown in FIG. 1) and an angle $\beta$ (as shown in FIG. 2) between a line extending from the bottom of the housing 2. The electrode 10, 10 may consist of an electrode base 11 and a sponge member 12 covering the electrode base 11 (as later described referring to FIGS. 4a, 4b and 5b, 5b). The entire electrode section 8 can be removed from the housing 2 if necessary (as shown in FIG. 3) and replaced with other electrode section. Set screws 13 are provided which connect the housing 2 with the electrode section 8.

FIG. 3 illlustrates a manner of detaching the housing 2 from the electrode section 8, in which 14 denotes an insert base of the electrode section 8 formed in a square having four sides sloping toward its end. The insert base 14 has at its end a plug 15 inserted into a fitting hole 14' and plug hole or receptacle 15', the plug 15 being provided with a guide groove 16 thereon. A hole 17 is formed in the insert base 14.

In the housing 2 shown in FIG. 3 is provided a fitting hole 14' and a plug hole or receptacle 15' as shown in dotted lines. When the housing 2 and the electrode section 8 are assembled, the insert base 14 with the plug 15 are pressed into the fitting hole 14' and plug hole or receptacle 15' in the housing 2. As the electrode section 8 is completely fitted to the housing 2, the hole 17 engages with a projection in the fitting hole, which projection is not shown in the drawing. The electrode section 8 may be securely engaged to the housing, thereby forming a complete electric connection between the housing and the electrode section 8.

Figure 4A:
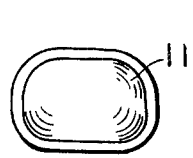
FIG. 4a is a plan view of the base part of the electrode section and FIG. 4b a front view of the base part of the electrode section.
Figure 4B:
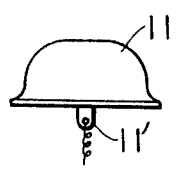

As shown in FIGS. 4a and 4b, the electrode base 11 may have a rectangular form as seen in plan view and a bowl shape in front elevation. The electrode base 11 may be provided with an electrode terminal 11' projecting from the bottom of the electrode base.

Figure 5A:
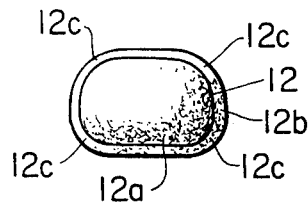
Figure 5B:
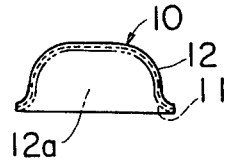

FIGS. 5a and 5b show a sponge member 12, which is similar in shape to that of FIGS. 4a and 4b. The sponge member is made of a sponge molding produced from a sponge plate pressed into a shape which conforms to the outer configuration of the electrode base. The sponge member 12 has a hollow space 12a to contain the electrode base 11 and also a peripheral portion 12b. For example, at four points on the peripheral portion 12b of the sponge member are provided an adhesive 12c which may be permeable, water-proof and rapid-curing. As the adhesive 12c on the peripheral portion 12b cures, the sponge member 12 is made non-collapsible even when it contains water. The sponge member 12 thus receives the above electrode base 11 for insertion into the hollow space 12a as shown by dotted lines on FIG. 5b to form the electrode 10.

Figure 6:
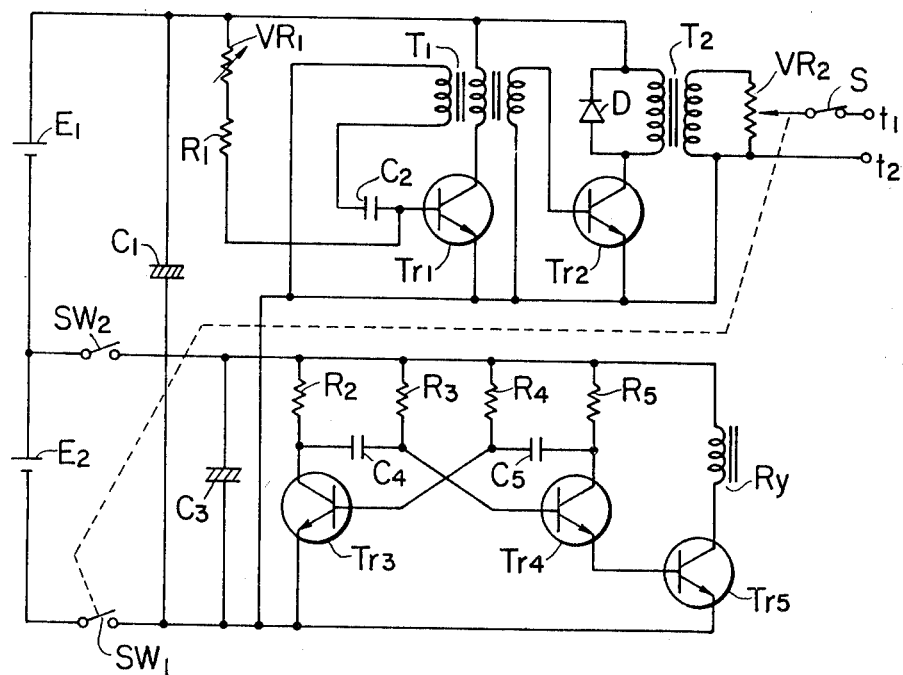
FIG. 6 is a diagrammatic view of an example of a low-frequency oscillating circuit used in the apparatus of the invention.

The low-frequency oscillating circuit contained in the housing 2 is shown in an embodiment of FIG. 6. Layer-built cells $E_1$ and $E_2$ supplying respectively a voltage of 9 volt are used for power source. The circuit contains in connection condensers $C_1 - C_5$; resistors $R_1 - R_5$; transistors $Tr_1 - Tr_5$; a germanium diode D; an oscillating transformer $T_1$; an output transformer $T_2$; variable resistors $VR_1$ and $VR_2$; switches $SW_1$ and $SW_2$; a lead relay $R_y$ with normally-closed contact S; and output terminals $t_1$ and $t_2$. In FIG. 6, the switches $SW_1$ and the variable resistor $VR_2$ are associated in operation. These correspond to the variable resistor 6 with output switch. The variable resistor $VR_1$ corresponds to the variable resistor 7 for adjustment frequency as shown in FIG. 1. Also the switch $SW_2$ in FIG. 6 corresponds to the slide switch in FIG. 1.

In operation, the switch $SW_1$ (variable resistor 6 with output switch) is set ON, then oscillation is produced by the transistor $Tr_1$ and oscillating transformer $T_1$, the output of which turns the transistor $Tr_2$ ON or OFF. Accordingly, electric current in the condenser $C_1$ loaded by series of cells $E_1$ and $E_2$ on the primary side of the output transformer $T_2$ instantly flows in the circuit and produces a large output on the secondary side. This output is produced from the variable resistor $VR_2$ and fed to the output terminals $t_1$ and $t_2$ (electrodes 10, 10) Therefore, if the variable resistor $VR_2$ (variable resistor 6 with output switch) is properly adjusted, a desired output can be obtained. The frequency of current may be adjusted only by turning the variable resistor $VR_1$ (variable resistor 7 for adjustment frequency). When the output is supplied intermittently, the switch $SW_2$ is closed. Then, as the transistors $Tr_3$ and $Tr_4$ form a nonstable multi-vibrator, the transistors are alternately turned ON or OFF. Therefore, the transistor $Tr_5$ is turned ON or OFF and the lead relay $R_y$ is energized and de-energized to set the normally-closed contact S ON or OFF, and the output of the output transformer $T_2$ is connected or disconnected under the control of the lead relay $R_y$. This electric operation will greatly add the stimulating effect to the muscles during the treatment.

Figure 6A:
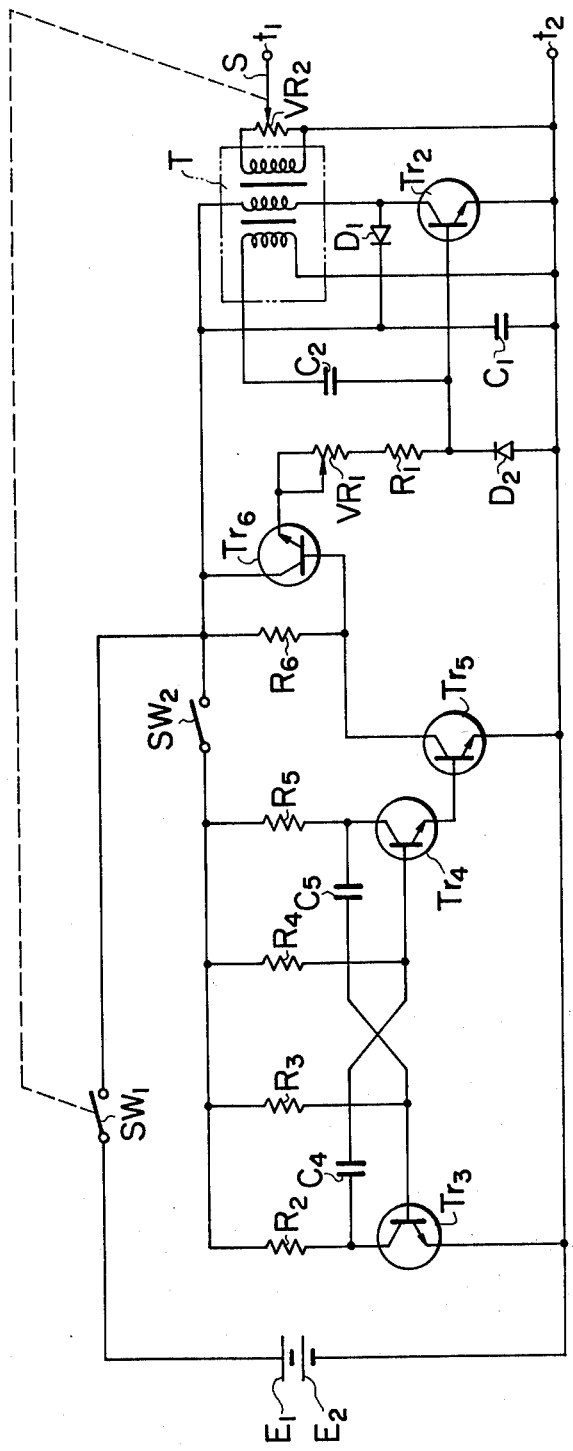
FIG. 6a is a low-frequency oscillating circuit of other embodiment used in the apparatus of the invention.

FIG. 6a is an embodiment of other circuit having an oscillating part (oscillating transformer $T_1$) and an output part (output transformer $T_2$) united into one as shown by T in FIG. 6. In this the cells $E_1$ and $E_2$ are connected in series serving as a power source for the whole circuit. In the circuit, $D_2$ is a protection diode for the transistor $Tr_2$. With the relay $R_y$ in FIG. 6 thus replaced with the transistor $Tr_6$, it is possible to lessen the power consumption and stabilize the operation of the whole circuit. $R_6$ is a bias resistance for the transistor $Tr_6$.

Figure 7:
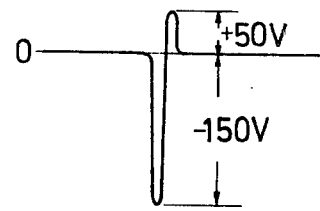

An example of the output wave is shown in FIG. 7. In the Figure, the output wave of positive polarity is relatively small, which is effected by the diode D or $D_1$ in the circuits and by which the pain in the muscles can be moderated when a current flows into the human body.

Example of a manner of practising the invention will now be described. First, as shown in FIG. 1, the sponge member 12 in the electrode section 8 may be soaked with water. The electrode section 8 with the sponge member containing water is pressed against the muscles. With the switch of the variable resistor 6 set ON, it may be gradually turned in the direction of the arrow as shown in FIG. 1. The variable resistor 6 may be turned round until the operator senses the stimulus most adapted for the parts to be treated in his body, and electricity is applied to the muscles producing a desired stimulus. When the slide switch 5 is turned in opposite direction relative to the position shown in FIG. 2, there is produced an intermittent charge of electricity in the muscles. In order to obtain much stronger stimulus in the muscles, the variable resistor 6 may be turned round in the arrow direction. The frequency of electric current wave may also be increased as desired by turning the variable resistor 7 in the direction of the arrow as shown in FIG. 1.

Figure 8A:
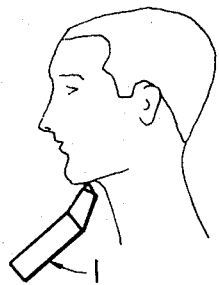
FIGS. 8a – 8h are views illustrating various modes of use of the apparatus of the invention.
Figure 8B:
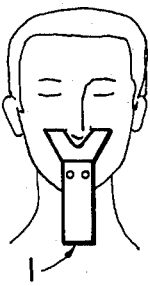
Figure 8C:
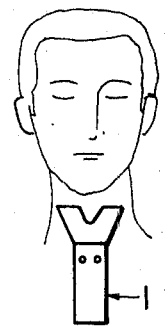
Figure 8D:
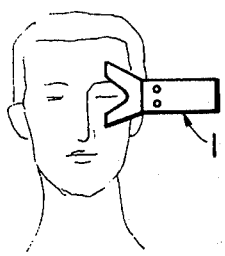
Figure 8E:
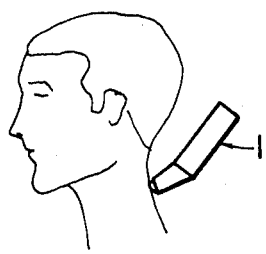
Figure 8F:
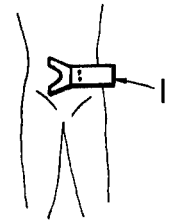
Figure 8G:
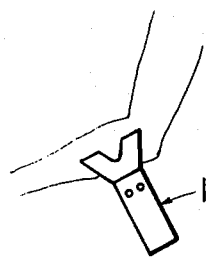
Figure 8H:
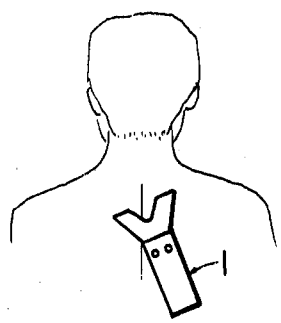

FIGS. 8a to 8h illustrate manners of application of the apparatus shown in FIG. 1 to various portions in the muscle of the body. FIG. 8a shows an example of application to the muscles in the jaw area. FIG. 8b shows the application to the muscles on both sides of the nose. Also, FIG. 8c shows the application to the throat; FIG. 8d in the upper and lower, and left and right sides of the eyes; FIG. 8e to the back of the head; FIG. 8f to the abdomen; FIG. 8g to the arms; and FIG. 8h to the back of the body, respectively. In FIG. 8h above, the apparatus can be operated by other person. Application of the apparatus is not limited only to such parts of the body as described but it can be used in any part of the body for the same treatment.

According to the invention, the apparatus may be operated such that when the housing 2 is held in the hand, the electrode 10, 10 may have a preferred angle with the object of treatment so that the electodes 10, 10 will adequately contact the muscles in any part of the body. The apparatus can be held in one hand so as to conveniently apply the electrodes 10, 10 to the muscles solely by operation of one hand.

As hereinbefore described, the electrode section can be advantageously detached and replaced with other type of the electrode section to enable one to perform a modified treatment of the muscles.

Examples of such modification are given in FIGS. 9, 10 and 11, which embody other types of the elctrode section. In the embodiment shown in FIG. 9, the electrodes 8A are formed in a bar-shape, at the ends of which is provided an electrode 10 having a sponge member 12 and in the middle of which is provided a metallic electrode 10' (this portion is gripped by hand). As the electrode 10 is applied to the muscles of a body, electric current is supplied to the body through a hand holding the metallic electrode 10'. This manner of application is suitable to provide stimulus locally in small parts of the body.

In FIGS. 10a and 10b, electrodes 8B are suitable for treatment in the muscles adjacent to the backbone. At the base 18 of the electrode section if formed two elevated areas or elevations to which are secured the electrodes 10, 10. This type of the apparatus is used more effectively on the back side of the body in a position that the operator lies on his back on the floor.

The electrodes 10, 10 in the electrode sections 8A, 8B in FIGS. 9 annd 10 are quite similar to that of the electrodes 10, 10 in FIG. 1.

FIG. 11 shows two eletrodes sections 8C, 8C formed in a metal plate defined by square frames 20, 20 which are also made of rubber to be convenient for use due to its flexibility. These electrodes 10'', 10'' have surfaces made of sheets of sponge 12', 12' capable of containing water to obtain better flexibility and electric charge.

It will be seen that the electrode sections 8A, 8B and 8C may preferably be provided with a cord connection 21 with the plug 15 that can be readily inserted into the housing 2.

What I claim is:

1. Apparatus for therapeutical treatment and stimulation of muscles using a low-frequency oscillator circuit, said apparatus comprising a hand-held housing containing a low-frequency oscillator circuit and a power source for said circuit comprising dry cells, an electrode section having two electrodes separated from each other, and a plug for detachably connecting said electrode section to the housing so as to complete an electrical connection between said electrodes and said oscillator circuit so that, in use of said apparatus, electric current is applied to the muscles of the human body so as to remedy pain and fatigue and strengthen the muscles by stimulation, said housing having a plug receptacle into which the plug of the electrode section is fitted, said electrode section including first and second outwardly extending arms arranged in a V-shaped configuration and forming an oblique angle with respect to said housing, each of said arms containing an electrode at the end thereof, each said electrode comprising a bowl-shaped sheet of metal and a sponge member of a shape conforming to the outer configuration of said bowl-shaped sheet adhesively secured thereto.

2. Apparatus for therapeutical treatment and stimulation of muscles using a low-frequency oscillator circuit, said apparatus comprising a hand-held housing containing a low-frequency oscillator circuit and a power source for said circuit comprising dry cells, an electrode section having two electrodes separated from each other, and a plug for detachably connecting said electrode section to the housing so as to complete an electrical connection between said electrodes and said oscillator circuit so that, in use of said apparatus, electric current is applied to the muscles of the human body so as to remedy pain and fatigue and strengthen the muscles by stimulation, said housing having a plug receptacle into which the plug of the electrode section is fitted, said electrode section having an elongated bar shape and including one electrode located at one end thereof and a sheet of metal located in the middle of the elongated bar shaped electrode section constituting the other electrode, said one electrode comprising a bowl-shaped sheet of metal and a sponge member of a shape conforming to the outer configuration of the bowl-shaped sheet adhesively secured thereto.

3. Apparatus for therapeutical treatment and stimulation of muscles using a low-frequency oscillator circuit, said apparatus comprising a hand-held housing containing a low-frequency oscilator circuit and a power source for said circuit comprising dry cells, an electrode section having two electrodes separated from each other, and a plug for detachably connecting said electrode section to the housing so as to complete an electrical connection between said electrodes and said oscillator circuit so that, in use of said apparatus, electric current is applied to the muslces of the human body so as to remedy pain and fatigue and strengthen the muscles by stimulation, said housing having a plug receptacle into which the plug of the electrode section is fitted, said electrode section including a base and first and second areas elevated from said base and spaced such that the elevated areas fit on opposite sides of the backbone of the human body, and each of the elevated areas including an electrode comprising a bowl-shaped sheet of metal and a sponge member of a shape conforming to the outer configuration of the bowl-shaped sheet adhesively secured thereto.

* * * * *